(12) United States Patent
Doty

(10) Patent No.: US 7,955,365 B2
(45) Date of Patent: *Jun. 7, 2011

(54) CLOSED LOOP CATHETER PHOTOPOLYMERIZATION SYSTEM AND METHOD OF TREATING A VASCULAR CONDITION

(75) Inventor: David R. Doty, Forestville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 912 days.

This patent is subject to a terminal disclaimer.

(21) Appl. No.: 11/279,021

(22) Filed: Apr. 7, 2006

(65) Prior Publication Data

US 2007/0237739 A1     Oct. 11, 2007

(51) Int. Cl.
*A61N 5/06* (2006.01)
(52) U.S. Cl. ............... 607/88; 606/15; 607/89; 604/20; 604/21
(58) Field of Classification Search .................. None
See application file for complete search history.

(56) References Cited

U.S. PATENT DOCUMENTS

| | | | |
|---|---|---|---|
| 3,429,313 A * | 2/1969 | Romanelli | 604/31 |
| 4,878,492 A * | 11/1989 | Sinofsky et al. | 606/7 |
| 5,328,471 A | 7/1994 | Slepian | |
| 5,612,050 A | 3/1997 | Rowe et al. | |
| 5,662,609 A | 9/1997 | Slepian | |
| 5,665,063 A * | 9/1997 | Roth et al. | 604/509 |
| 5,698,189 A | 12/1997 | Rowe et al. | |
| 5,779,673 A * | 7/1998 | Roth et al. | 604/101.03 |
| 6,004,547 A | 12/1999 | Rowe et al. | |
| 6,287,320 B1 | 9/2001 | Slepian | |
| 6,468,520 B1 | 10/2002 | Rowe et al. | |
| 2007/0010782 A1* | 1/2007 | Doty et al. | 604/20 |

* cited by examiner

*Primary Examiner* — Henry M Johnson, III
*Assistant Examiner* — Lynsey Crandall

(57) ABSTRACT

A photopolymerization system includes a catheter having a proximal inflatable member, a distal inflatable member, a fluid delivery lumen, and a fluid drainage lumen. The fluid delivery lumen includes at least one delivery port and the fluid drainage lumen at least one drainage port. The ports are positioned between the proximal inflatable member and the distal inflatable member. A light emission member is positioned adjacent the catheter. In a method of treating a vascular condition, the catheter is delivered to a treatment site within a vessel. The first and second inflatable members are expanded to form an enclosed treatment space within the vessel. Fluid is delivered to the treatment space through fluid delivery lumen. Excess fluid is removed from the treatment space through the fluid drainage lumen. The treatment space is exposed to light. A portion of the fluid is polymerized within the treatment space upon exposure to the light.

14 Claims, 3 Drawing Sheets

CLOSED LOOP CATHETER PHOTOPOLYMERIZATION SYSTEM AND METHOD OF TREATING A VASCULAR CONDITION

TECHNICAL FIELD OF THE INVENTION

This invention relates generally to biomedical systems for treating vascular conditions. More specifically, the invention relates to a closed loop catheter photopolymerization system and method of treating a vascular condition.

BACKGROUND OF THE INVENTION

Photopolymerization, i.e., polymerization induced by light, is used to convert a liquid monomer or macromer to a polymer using visible or ultraviolet radiation. Some types of cross-linked hydrophilic polymers known as hydrogels may be formed in vivo using photopolymerization. These hydrogels exhibit good biocompatibility, making them attractive materials for use in a variety of biomedical applications.

Formation of photopolymerized hydrogels in vivo can be accomplished using bulk or interfacial photopolymerization. In bulk photopolymerization, a photoinitiator is dissolved in a hydrogel precursor (prepolymer) solution. A photoinitiator is a material that has a high absorption at a specific wavelength of light to produce radical initiating species that convert a prepolymer to a polymer. Upon exposure to an appropriate wavelength of light, the hydrogel precursor and photoinitiator solution is converted to the hydrogel state.

In interfacial photopolymerization, a photoinitiator is adsorbed onto the surface of tissues or cells. Eosin photoinitiators are commonly used because of their high affinity for tissues. A prepolymer, in this case a hydrogel precursor solution, is then delivered to the site, and the site is exposed to an appropriate light source. Polymerization occurs at the tissue interface, where the hydrogel precursor is in contact with the adsorbed photoinitiator.

Interfacial photopolymerization may be used to form thin hydrogel linings on various tissue surfaces, including the inner walls of vessels carrying bodily fluids. Dual occlusion catheters are currently used over standard guidewires to deliver photoinitiators and prepolymers to target vessels. Because a typical dual occlusion catheter requires a separate inflation lumen for each balloon, the catheter is bulky, having an undesirably large crossing profile. In addition, as currently performed, the photopolymerization procedure requires that the guidewire over which the catheter is delivered be withdrawn prior to activating the prepolymer using a light source. If left in place, the guidewire produces a shadow on the wall of the vessel, resulting in incomplete coverage of the vessel with a polymer coating. The additional step of withdrawing the guidewire adds to the time required to perform the photopolymerization procedure, posing some risk that the vessel may be damaged or other complications may occur.

Therefore, it would be desirable to have an improved catheter-based photopolymerization system and treatment method that overcomes the aforementioned and other disadvantages.

SUMMARY OF THE INVENTION

A first aspect according to the invention provides a photopolymerization system. The system includes a catheter having a proximal inflatable member, a distal inflatable member, a fluid delivery lumen, and a fluid drainage lumen. The fluid delivery lumen includes at least one delivery port and the fluid drainage lumen includes at least one drainage port. The ports are positioned between the proximal inflatable member and the distal inflatable member. A light emission member is positioned adjacent the catheter.

A second aspect according to the invention provides a method of treating a vascular condition. A catheter is delivered to a treatment site within a vessel. The catheter includes a proximal inflatable member, a distal inflatable member, a fluid delivery lumen, and a fluid drainage lumen. The first and second inflatable members are expanded to form an enclosed treatment space within the vessel. Fluid is delivered to the treatment space through fluid delivery lumen. Excess fluid is removed from the treatment space through the fluid drainage lumen. The treatment space is exposed to light. A portion of the fluid is polymerized within the treatment space upon exposure to the light.

A third aspect according to the invention provides a photopolymerization system that includes catheter means for occluding a vessel at a treatment site and means for delivering a fluid to the treatment space. The system further includes means for removing excess fluid from the treatment space and means for exposing the treatment space to light.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

Like reference numbers are used throughout the drawings to refer to like elements.

DESCRIPTION OF THE PRESENTLY PREFERRED EMBODIMENTS

Figure 1:
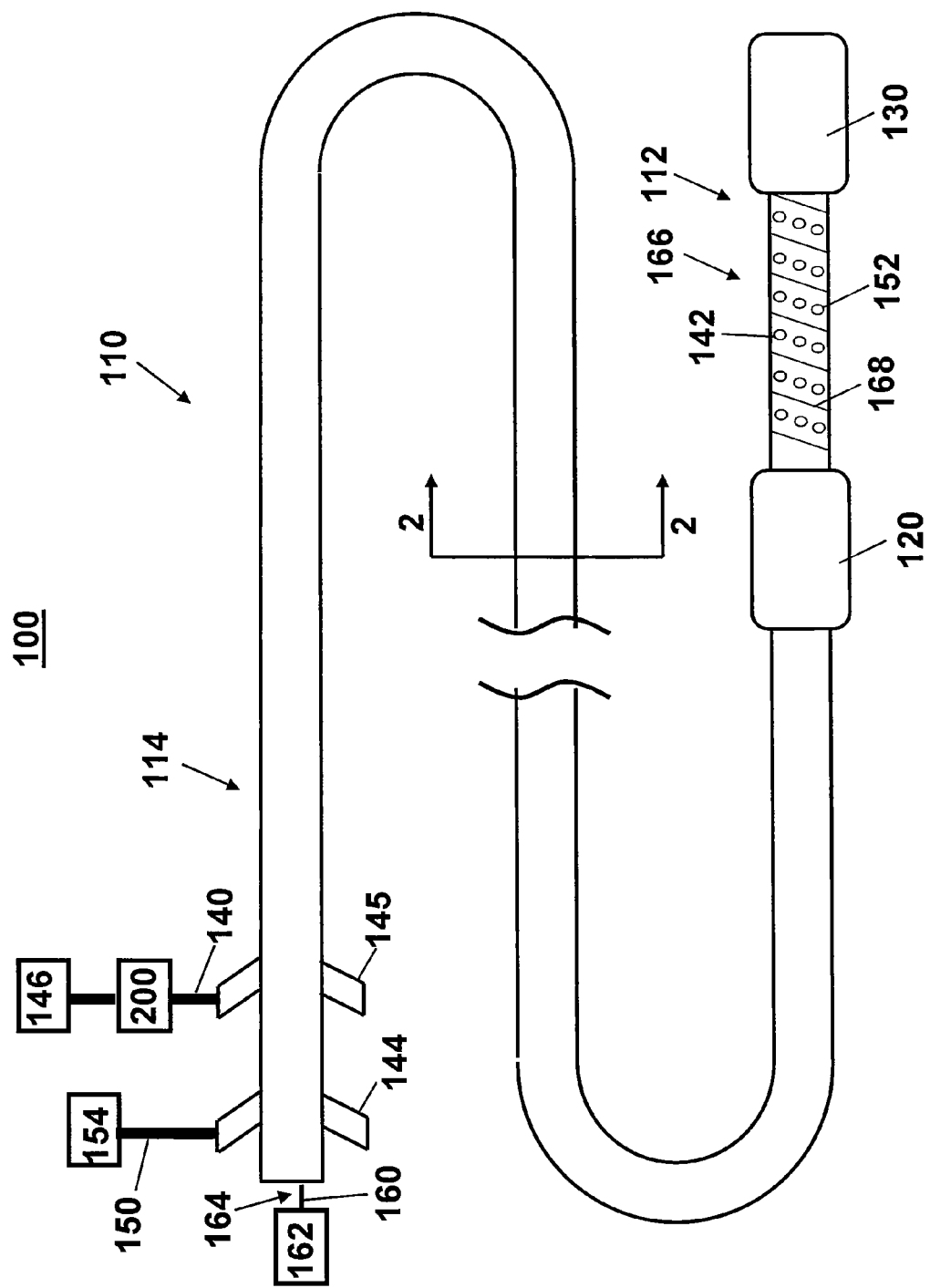
FIG. 1 is an illustration of one embodiment of a system for treating a vascular condition, in accordance with the present invention, showing the system as it would appear when partially delivered to a treatment site within a vessel.

One aspect of the present invention is a photopolymerization system for treating a vascular condition. The system, illustrated in FIGS. 1 and 2 at 100, includes a catheter 110 having a proximal inflatable member 120, a distal inflatable member 130, a fluid delivery lumen 140, and a fluid drainage lumen 150. Fluid delivery lumen 140 includes at least one delivery port 142 and the fluid drainage lumen 150 includes at least one drainage port 152. Ports 142, 152 are positioned between the proximal inflatable member 120 and the distal inflatable member 130. A light emission member 160 is positioned adjacent the catheter 110.

In one embodiment, light emission member 160 is an optical fiber operably connected to a light source 162 at a proximal portion 164 and abraded at a distal portion 166. Proximal portion 164 is substantially straight along the length of catheter 110 terminating adjacent a connector arm of a luer 144. Light is transmitted from the light source 162 through the light emission member 160 from the luer 144 to the abraded distal portion 166. Abraded distal portion 166 provides a uniform diffusion of light at a treatment site. In one embodiment, light emission member 160 comprises a coil 168 formed at the distal portion 166 of the optical fiber. In another embodiment, the distal portion 166 of the light emission member 160 may be a section of an optical fiber that is treated in another manner to diffuse light from the fiber. In still another embodiment, the distal portion 166 may be any material capable of emitting the desired intensity of light and may be operably connected to a light source by any means of conveying light to the coil.

In one embodiment, the light emission member 160 is positioned substantially within the catheter 110. Specifically, the proximal portion 164 of the light emission member 160 is positioned within a light emission lumen formed in the catheter 110. In another embodiment, the proximal portion 164 of the light emission member 160 is positioned outside of the catheter 110 thereby eliminating the need for the light emission lumen. Those skilled in the art will appreciate that the light emission member may vary from the illustrated and described embodiments, including future innovations, without departing from the spirit and scope of the present invention. Further, the number of light emission members may be varied, with a different number of emission members being distributed about the distal portion 166.

In one embodiment, multiple delivery ports 142 and drainage ports 152 are distributed about the circumference of a distal portion 112 of the catheter 110 in a pattern that allows the ports 142, 152 to be interspaced with (i.e., positioned between) individual loops of the light emission member 160. Coil 168 loops are positioned on the distal portion 112 such that they do not block the delivery and drainage ports 142, 152. Delivery and drainage ports 142, 152 are formed in distal portion 112 by, for example, drilling or laser cutting. Delivery ports and drainage ports 142, 152 are substantially circular openings having a diameter of about 0.010 inch. As will be apparent to one skilled in the art, the number, size, and shape of the delivery and drainage ports may be varied as needed. For example, the number of openings chosen may depend on the length of distal portion 112. In an alternative embodiment, the delivery ports may be vertical slots, horizontal slits, and the like.

In one embodiment, a check valve assembly 200 is operably connected to the fluid delivery lumen 140. Check valve assembly 200 comprises any valve or manifold known in the art for controlling pressure through the fluid delivery lumen 140. A pump assembly 154 is operably connected to the fluid drainage lumen 150 via the luer 144. Pump assembly 154 provides a vacuum to the fluid drainage lumen 150 to augment drainage of fluid through the at least one drainage port 152.

In one embodiment, system 100 is used to apply a polymer coating to the inner surface of a blood vessel or other vessel by interfacial photopolymerization using a photoinitiator and prepolymer. To prevent formation of a polymer coating on an exterior surface of the catheter 110, the distal portion 112 may include and/or be covered with a material that does not absorb or otherwise retain the photoinitiator and prepolymer.

Figure 2:
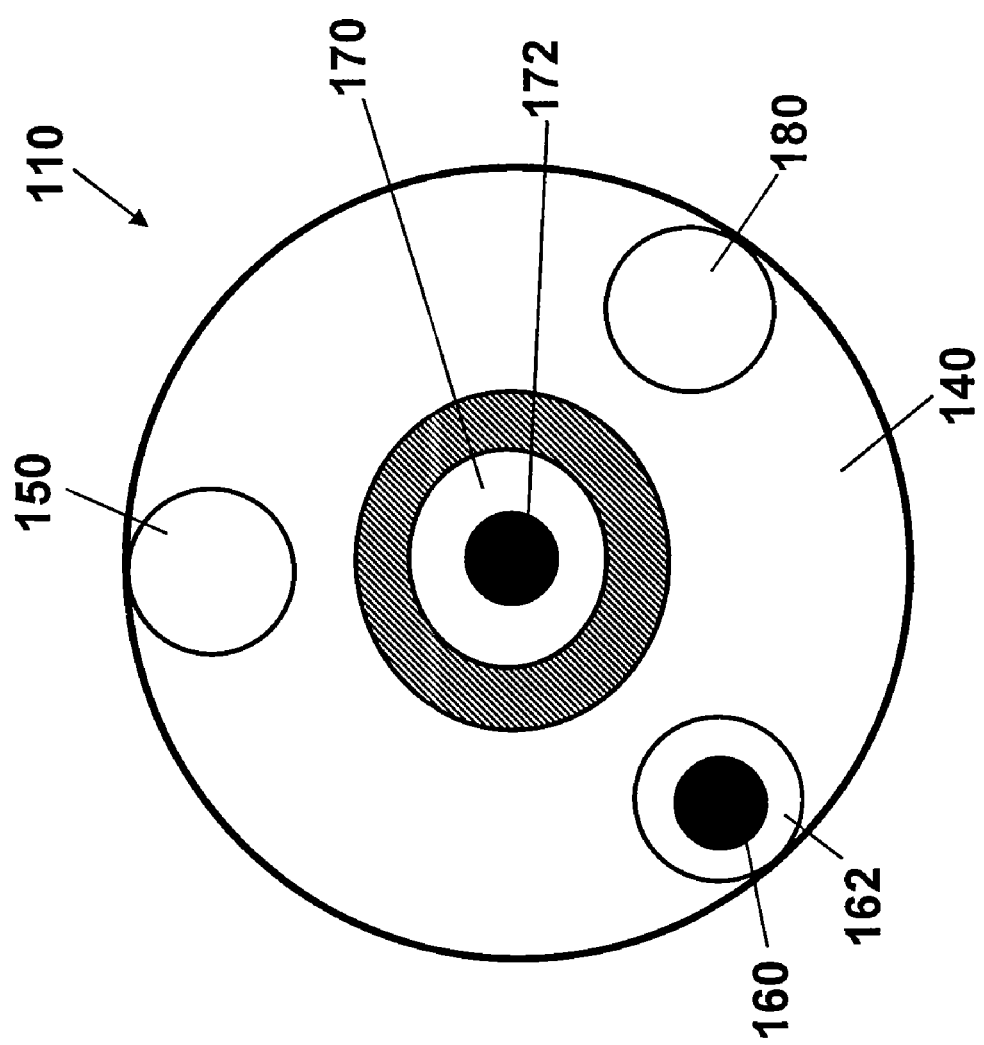
FIG. 2 is an enlarged cross-sectional view of a segment of the system of FIG. 1.

As shown in FIG. 2, which is a cross-sectional view of one embodiment of a segment of system 100, catheter 110 includes five lumens: the fluid delivery lumen 140, fluid drainage lumen 150, light emission lumen 162, a guidewire lumen 170, and an inflation lumen 180.

Referring also to FIG. 1, the fluid delivery lumen 140 extends from a luer 145 positioned adjacent to a proximal portion 114 of the catheter 110 to a location adjacent to the distal portion 112 of catheter 110 terminating at the delivery ports 142. Fluid delivery lumen 140 is in fluid communication with the delivery ports 142, luer 145, and a fluid supply 146. Fluid supply 146 may be, for example, a syringe operated manually by an operator. Fluid supply 142 is a supply of at least one fluid selected from a group consisting of a photoinitiator, a prepolymer, and a flushing solution, such as Ringer's or saline solution. The term "prepolymer" is used herein to refer to any monomer, macromer, or polymer that is converted by photopolymerization in the presence of a photoinitiator and light to a polymer coating.

Fluid drainage lumen 150 extends from luer 144 adjacent to the proximal portion 114 of the catheter 110 to a location adjacent to the distal portion 122 of the catheter 110 terminating at the drainage ports 152. Fluid drainage lumen 150 is in fluid communication with the drainage ports 152, luer 144, and pump assembly 154. Light emission lumen 162 extends from the proximal portion 114 of the catheter 110 to a location adjacent to the distal portion 112 of the catheter 110. Guidewire lumen 170 extends the length of catheter 110 to permit the catheter 110 to be delivered to the treatment site over a guidewire 172. Guidewire 172 may be, for example, a nitinol or stainless steel hypotube. Catheter 110 may include one or more radiopaque marker(s) (not shown) to aid positioning at the treatment site. Guidewire 172 is first placed in a proper position for treating the vessel before the catheter 110 is advanced to the treatment site.

Inflation lumen 180 opens from luer 145 into proximal and distal inflatable members 120, 130 to permit expansion. Proximal and distal inflatable members 120, 130 are shown in a deflated configuration in FIG. 1. Proximal inflatable member 120 is disposed on catheter 110 proximal to the distal inflatable member 130. Proximal and distal inflatable members 120, 130 may be any inflatable members known in the art that are appropriate for occluding a vessel, for example a balloon made of a biocompatible material such as polyethylene, polyethylene terephthalate (PET), polyurethane, an elastomeric balloon material, or the like. To prevent formation of a polymer coating on the exterior of the proximal and distal inflatable members 120, 130 may comprise a material that does not absorb or otherwise retain the photoinitiator and prepolymer.

After inflation, the proximal and distal inflatable members 120, 130 form an enclosed treatment space within the vessel. In one embodiment, a photoinitiator is delivered to the treatment space via fluid delivery lumen 140 and delivery ports 142. Distal inflatable member 130 acts as a fluid barrier to partially seal the treatment space while still allowing fluid to pass beyond the balloon as pressure builds up within the treatment space. Thus, distal inflatable member 130 creates backpressure, ensuring the treatment space becomes filled with a fluid. Distal inflatable member 130 is capable of partially collapsing to allow a minimal amount of fluid to exit the treatment space as needed. Proximal inflatable member 120 may be formed using a less malleable material than that used to form distal inflatable member 130 to ensure fluid exits the distal end of the treatment space.

Once the photoinitiator in contact with the vessel wall is adsorbed on (or is otherwise bound to) the tissue of the vessel wall, excess photoinitiator is flushed from the treatment space using a saline or other flushing solution. The prepolymer is then delivered to the treatment space until it fills the space. The light source operably connected to coil 168 is then activated, causing the coil to deliver light to the vessel wall, thereby curing the prepolymer and forming a polymer (typically a hydrogel) coating on the wall of the vessel. The proximal and distal inflatable members 120, 130 may then be deflated, allowing uncured material to be washed away as the inflatable members 120, 130 contract away from the wall of the vessel. Alternatively, uncured material may be removed prior to deflation by, for example, providing a vacuum to the fluid drainage lumen 150 and additionally providing a flushing solution to the treatment site. System 100 may then be withdrawn from the vessel.

Another system for treating a vascular condition comprises catheter means for occluding a vessel at a treatment site, means for delivering a fluid to the treatment space, means for removing excess fluid from the treatment space, and means for exposing the treatment space to light.

The catheter means for occluding a vessel distal at a treatment site may include proximal and distal inflatable members as described above and illustrated in FIGS. 1 and 2 at 120 and 130. Alternatively, the means may include any structure presently existing or developed in the future that is appropriate for being carried on a catheter and occluding a vessel, such as, an expandable structure that includes ribs and an outer covering, an expandable shape-memory structure having an outer covering, or an umbrella-like structure.

The means for delivering a fluid to the treatment site may be a fluid delivery lumen such as is described above and illustrated in FIG. 2 at 140. Alternatively, the means may be any lumen connecting a fluid source with a treatment area formed between the two occlusion means.

The means for removing excess fluid from the treatment space may be a fluid drainage lumen such as is described above and illustrated in FIG. 2 at 150. Alternatively, the means may be any lumen connecting a vacuum generator with a treatment area formed between the two occlusion means.

The means for exposing the treatment space to light may be a light emission coil such as is described above and illustrated in FIG. 1 at 168. Alternatively, the means may be any structure presently existing or developed in the future that performs the same function.

One skilled in the art will appreciate that, while described above in the context of forming a coating on the inner surface of a vessel, a system in accordance with the present invention may be used for other applications. For example, a coating may be formed on all or part of the inner surface of a treatment device such as a stent or graft positioned within the vessel, or on an inner surface of at least a portion of both the vessel and a treatment device. Further, the system may be used to deliver and activate materials other than photopolymerization materials, including, but not limited to, a photoactivated drug or other therapeutic agent.

Figure 3:
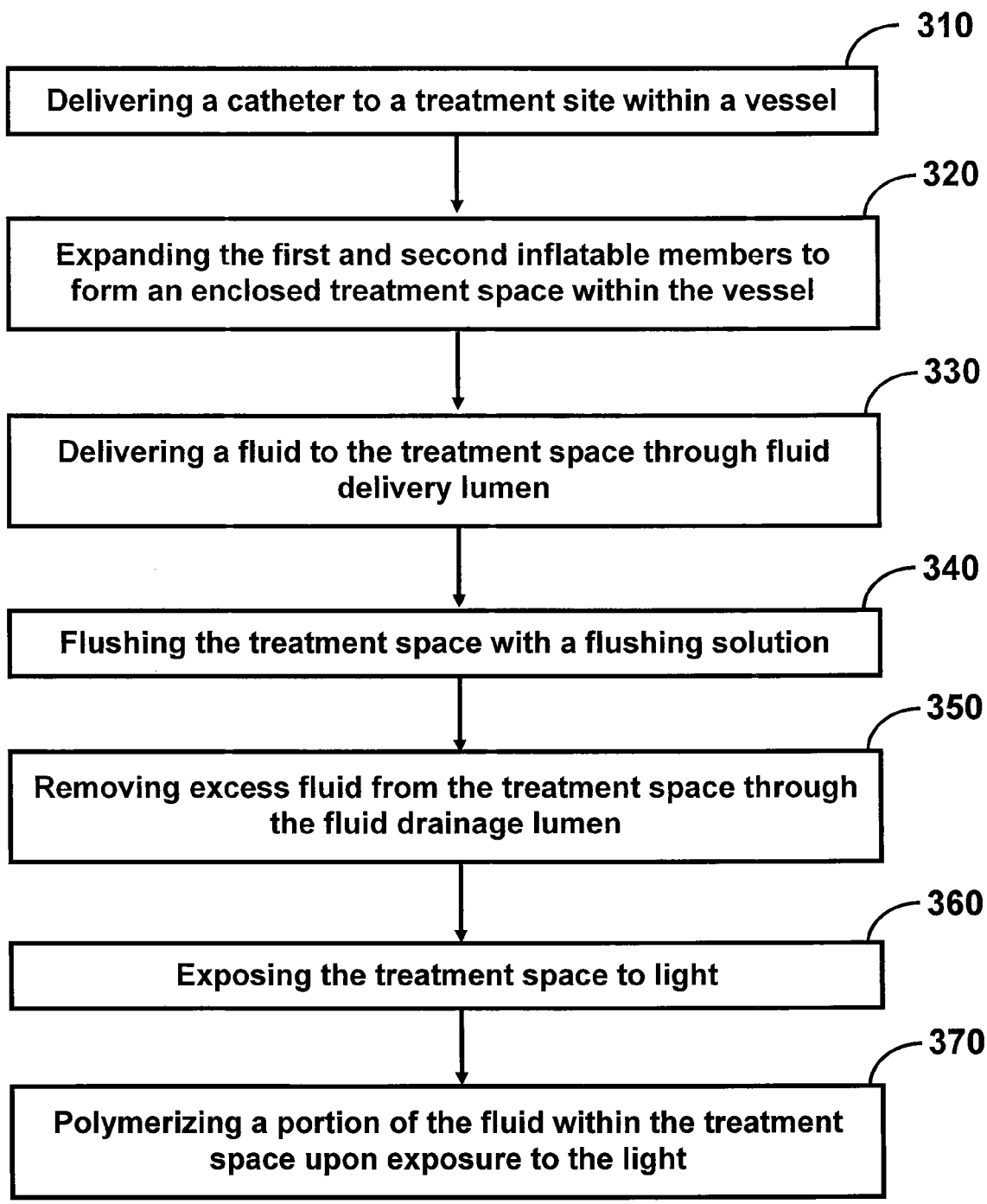
FIG. 3 is a flow diagram of one embodiment of a method of treating a vascular condition, in accordance with the present invention.

Another aspect of the present invention is a method of treating a vascular condition. FIG. 3 shows a flow diagram of one embodiment of the method in accordance with the present invention.

A catheter is delivered to a treatment site (Block 310). The catheter may be as described above and illustrated in FIGS. 1 and 2. The catheter includes a proximal inflatable member, a distal inflatable member, a fluid delivery lumen, and a fluid drainage lumen. The catheter may be delivered over a propositioned guidewire to the treatment site.

The first and second inflatable members are expanded to form an enclosed treatment space within the vessel (Block 320). This may be accomplished as described previously. One skilled in the art will appreciate that the order of inflating the inflatable members may be varied. In addition, inflatable members other than balloons may be used, with the inflatable members being expanded by means other than inflation.

Fluid is delivered to the treatment space through the fluid delivery lumen (Block 330). Fluid may be a photoinitiator, a prepolymer, and/or a flushing solution. In one embodiment, flushing solution may be delivered to the treatment site to flush the vessel of blood (Block 340), followed by a photoinitiator, flushing solution to flush the vessel of photoinitiator, and then a prepolymer. Fluid may be delivered to the treatment site circumferentially via fluid delivery lumen 140. The pressure of the fluid through the fluid delivery lumen 140 may be controlled via a check valve assembly 200 operably connected to the fluid delivery lumen 140.

Excess fluid is removed from the treatment space through the fluid drainage lumen (Block 350). Excess fluid may be removed from the treatment via fluid drainage lumen 150. A vacuum may be provided to the fluid drainage lumen 150 with the pump assembly 154 to assist drainage.

The treatment space is exposed to light (Block 360). In the present embodiment, light is conveyed to the coil 168 via the proximal portion 164 of the optical fiber. The intensity and wavelength of the administered light is dependent upon the nature of the photoinitiator and the prepolymer and can be determined by one skilled in the art. The light forms a helical path defined by the loops of the coil 168. Alternatively, the catheter 110 may include a plurality of linear fiber optic members spaced apart at the distal portion 166 of the optical fiber. The multiple liner fiber optic members form longitudinal paths that are substantially parallel and spaced to ensure adequate exposure of the treatment space.

A portion of the fluid is polymerized within the treatment space upon exposure to the light (Block 370). As the light is emitted by the coil 168 or by the plurality of linear fiber optic members, the prepolymer in contact with tissue to which photoinitiator has been bound is cured or polymerized to form a polymer (typically a hydrogel) coating on the inner wall of the vessel. Once the polymer coating has been formed, the inflatable members may be returned to their unexpanded configurations, and the catheter and the guidewire may be withdrawn from the vessel, either individually or together.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

The invention claimed is:

1. A photopolymerization system comprising:
a catheter including a proximal inflatable member, a distal inflatable member, a fluid delivery lumen, and a fluid drainage lumen; wherein the fluid delivery lumen includes at least one delivery port and the fluid drainage lumen includes at least one drainage port, said ports positioned between the proximal inflatable member and the distal inflatable member; and
a light emission member comprising a coil positioned on an outermost surface of the catheter between the proximal inflatable member and the distal inflatable member wherein the light emission member is directly exposed to a vessel wall when the catheter is deployed at a treatment site and the proximal inflatable member and the distal inflatable member are inflated.

2. The system of claim 1 wherein the catheter includes an inflation lumen and a guidewire lumen.

3. The system of claim 1 wherein the at least one delivery port is distributed about the circumference of a distal portion of the catheter.

4. The system of claim 1 wherein the fluid delivery lumen is in fluid communication with a fluid supply.

5. The system of claim 4 wherein the fluid supply is a supply of at least one fluid selected from a group consisting of a photoinitiator, a prepolymer, and a flushing solution.

6. The system of claim 1 wherein the light emission member is positioned substantially within the catheter.

7. The system of claim 1 further comprising a check valve assembly operably connected to the fluid delivery lumen.

8. A method of treating a vascular condition, the method comprising:
   delivering a catheter to a treatment site within a vessel, the catheter including a proximal inflatable member, a distal inflatable member, a fluid delivery lumen, a fluid drainage lumen, and a light emission member comprising a coil positioned on an outermost surface of the catheter between the proximal inflatable member and the distal inflatable member;
   expanding the proximal and distal inflatable members to form an enclosed treatment space within the vessel at the treatment site;
   delivering a fluid to the treatment space through the fluid delivery lumen;
   removing excess fluid from the treatment space through the fluid drainage lumen;
   exposing the treatment space directly to light from the light emission member; and
   polymerizing a portion of the fluid within the treatment space upon exposure to the light.

9. The method of claim 8 wherein the fluid is selected from a group selected from a photoinitiator, a prepolymer, and a flushing solution.

10. The method of claim 8 wherein the fluid is delivered circumferentially.

11. The method of claim 8 wherein the treatment space is exposed to light along a helical path.

12. The method of claim 8 further comprising flushing the treatment space with a flushing solution.

13. The system of claim 1 wherein the coil is a coil of abraded optical fiber.

14. The method of claim 8 wherein the coil is a coil of abraded optical fiber.

* * * * *